United States Patent
Nakagawa et al.

(10) Patent No.: US 9,709,497 B2
(45) Date of Patent: Jul. 18, 2017

(54) TRANSIENT ABSORPTION MEASUREMENT METHOD AND TRANSIENT ABSORPTION MEASUREMENT APPARATUS

(71) Applicant: UNISOKU CO., LTD., Hirakata-shi, Osaka (JP)

(72) Inventors: Tatsuo Nakagawa, Hirakata (JP); Kido Okamoto, Hirakata (JP); Hiroaki Hanada, Hirakata (JP)

(73) Assignee: UNISOKU CO., LTD., Osaka (JP)

( * ) Notice: Subject to any disclaimer, the term of this patent is extended or adjusted under 35 U.S.C. 154(b) by 0 days.

(21) Appl. No.: 15/358,313

(22) Filed: Nov. 22, 2016

(65) Prior Publication Data

US 2017/0074794 A1  Mar. 16, 2017

Related U.S. Application Data

(63) Continuation of application No. PCT/JP2015/064390, filed on May 20, 2015.

(30) Foreign Application Priority Data

May 22, 2014  (JP) .................. 2014-106109

(51) Int. Cl.
*G01N 21/00* (2006.01)
*G01N 21/59* (2006.01)
*G01N 21/27* (2006.01)

(52) U.S. Cl.
CPC ............. *G01N 21/59* (2013.01); *G01N 21/27* (2013.01)

(58) Field of Classification Search
CPC .. G02B 26/127; G02B 21/361; G02B 26/101; G02B 26/105; G02B 26/12;
(Continued)

(56) References Cited

U.S. PATENT DOCUMENTS 5,706,094 A * 1/1998 Maris ................. G01N 21/1717
356/432
5,748,318 A * 5/1998 Maris ................. G01N 21/1702
356/630
(Continued)

FOREIGN PATENT DOCUMENTS

JP  61-026842 A  2/1986
JP  63-313036 A  12/1988
(Continued)

OTHER PUBLICATIONS

E. C. Carroll et al., "A single source femtosecond-millisecond broadband spectrometer," Review of Scientific Instruments, 2009, pp. 1-3, vol. 80.
(Continued)

*Primary Examiner* — Michael P Stafira
(74) *Attorney, Agent, or Firm* — Sughrue Mion, PLLC

(57) ABSTRACT

By use of a pump light source for repeatedly generating a pump light pulse and a probe light source for repeatedly generating a probe light pulse in a shorter repetition time interval than the pump light pulse, the pump light pulse is repeatedly irradiated on a sample, and the probe light pulse is repeatedly irradiated on the sample every time the pump pulse is irradiated. An intensity of a probe light pulse having passed through the sample is detected. A shift in a delay time of the probe light pulse with respect to the pump light pulse is measured every time the pump light pulse is irradiated. Transient absorption measurement data of the sample is obtained based on the detected data of the probe light pulse intensity obtained in higher time density than repetition time density of the probe light pulse based on the measured shift in the delay time.

13 Claims, 9 Drawing Sheets

(58) Field of Classification Search
CPC .... G02B 26/123; G02B 21/244; G02B 21/26; G02B 21/365; G02B 21/002; G02B 21/0036; G02B 21/008; G02B 21/34; G02B 13/08

See application file for complete search history.

(56) References Cited

U.S. PATENT DOCUMENTS

| | | | |
|---|---|---|---|
| 2008/0251740 | A1 | 10/2008 | Dilhaire et al. |
| 2009/0236501 | A1 | 9/2009 | Takahashi et al. |
| 2010/0294934 | A1* | 11/2010 | Hashimoto ........ G01N 21/3581 250/338.1 |

FOREIGN PATENT DOCUMENTS

| | | |
|---|---|---|
| JP | 11-511240 A | 9/1999 |
| JP | 2003-035665 A | 2/2003 |
| JP | 2007-212145 A | 8/2007 |
| JP | 2009-512848 A | 3/2009 |
| JP | 2009-229247 A | 10/2009 |
| WO | 97/08536 A1 | 3/1997 |
| WO | 99/13318 A1 | 3/1999 |

OTHER PUBLICATIONS

Bernhard Lang et al., "Broadband ultraviolet-visible transient absorption spectroscopy in the nanosecond to microsecond time domain with sub-nanosecond time resolution," Review of Scientific Instruments, 2013, pp. 1-8, vol. 84.

Andrew R. Cook et al., "Optical fiber-based single-shot picosecond transient absorption spectroscopy," Review of Scientific Instruments, 2009, pp. 1-7, No. 80.

Paul A. Elzinga et al., "Pump/Probe Spectroscopy by Asynchronous Optical Sampling," Applied Spectroscopy, 1987, pp. 2-4, No. 41, No. 1.

Laura Antonucci et al., "Asynchronous optical sampling with arbitrary detuning between laser repetition rates," Optics Express, Jul. 30, 2012, pp. 17928-17937, vol. 20, No. 16.

Laura Antonucci et al., "Arbitrary-detuning asynchronous optical sampling pump-probe spectroscopy of bacterial reaction centers," Optics Letters, Sep. 1, 2013, pp. 3322-3324, vol. 38, No. 17.

Laura Antonucci et al., "Arbitrary-detuning asynchronous optical sampling with amplified laser systems," Optics Express, Oct. 14, 2015, pp. 27931-27940, vol. 23, No. 21.

Tatsuo Nakagawa et al., "Oral: A Novel Technique to Measure Transient Absorption, RIPT Method, Covering from Sub-Nanosecond to Millisecond Time Region," Inventor's article applied for the proceedings of an international conference, ICP2015 held in Jun. 2015, sent to conference authority on Mar. 15, 2015.

Tatsuo Nakagawa et al., "A Novel Technique to Measure Transient Absorption RIPT method Covering from Sub-Nanosecond to Millisecond Time Region," PowerPoint Presentation presented at the international conference ICP2015 on Jun. 29, 2015.

Japanese Notification of Reasons for Rejection issued in JP 2014-106109 dated Jul. 24, 2015.

Japanese Notification of Reasons for Rejection issued in JP 2014-106109 dated Oct. 14, 2015.

Japanese Notice of Allowance issued in JP 2014-106109 dated Dec. 18, 2015.

Written Opinion of the International Searching Authority of PCT/2015/064390 dated Jul. 28, 2015.

International Search Report of PCT/JP2015/064390 dated Jul. 28, 2015.

* cited by examiner

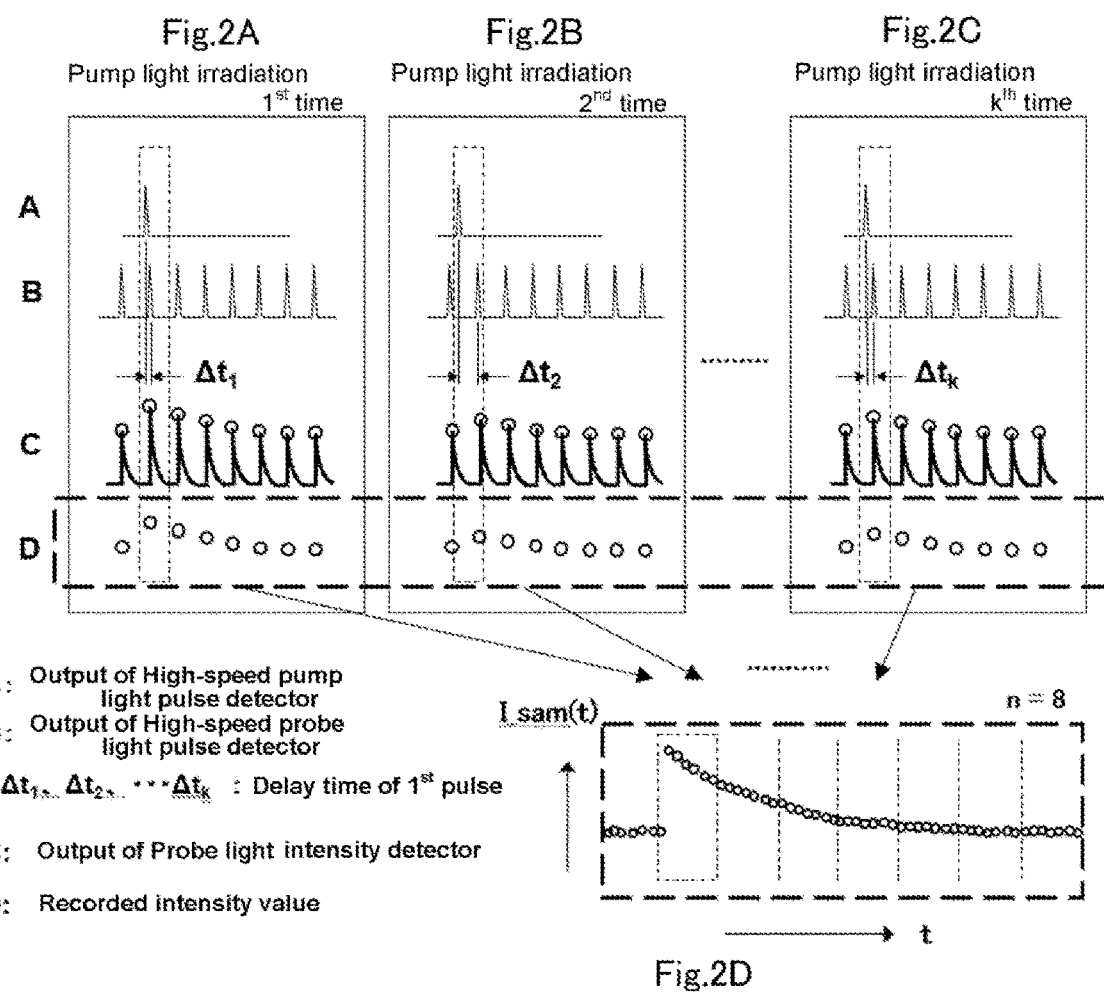

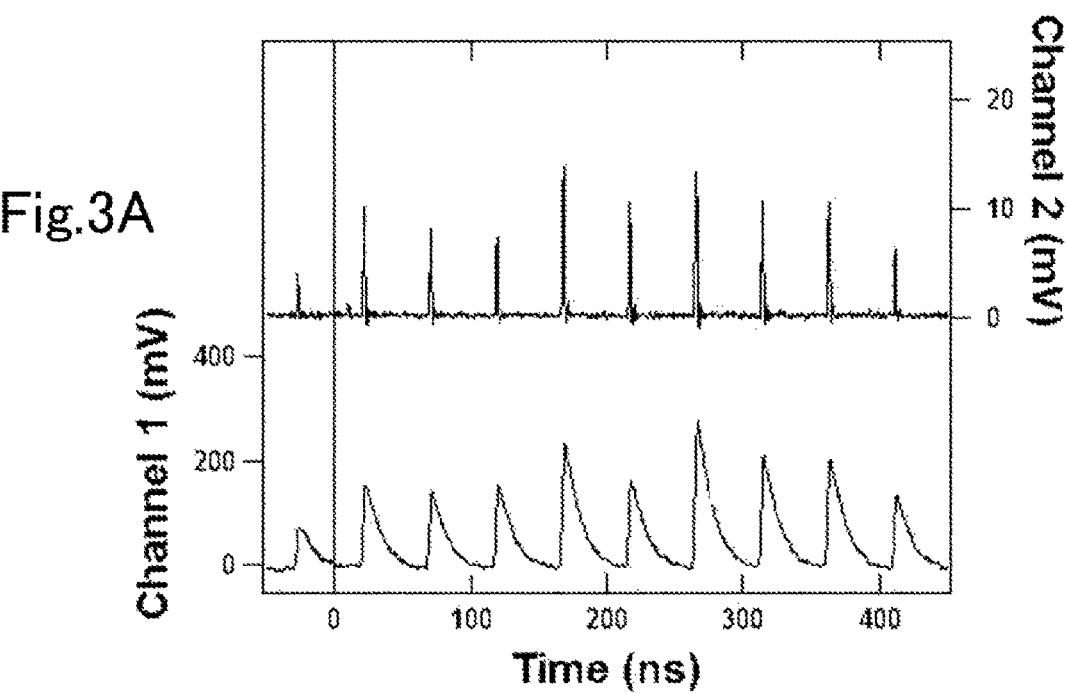
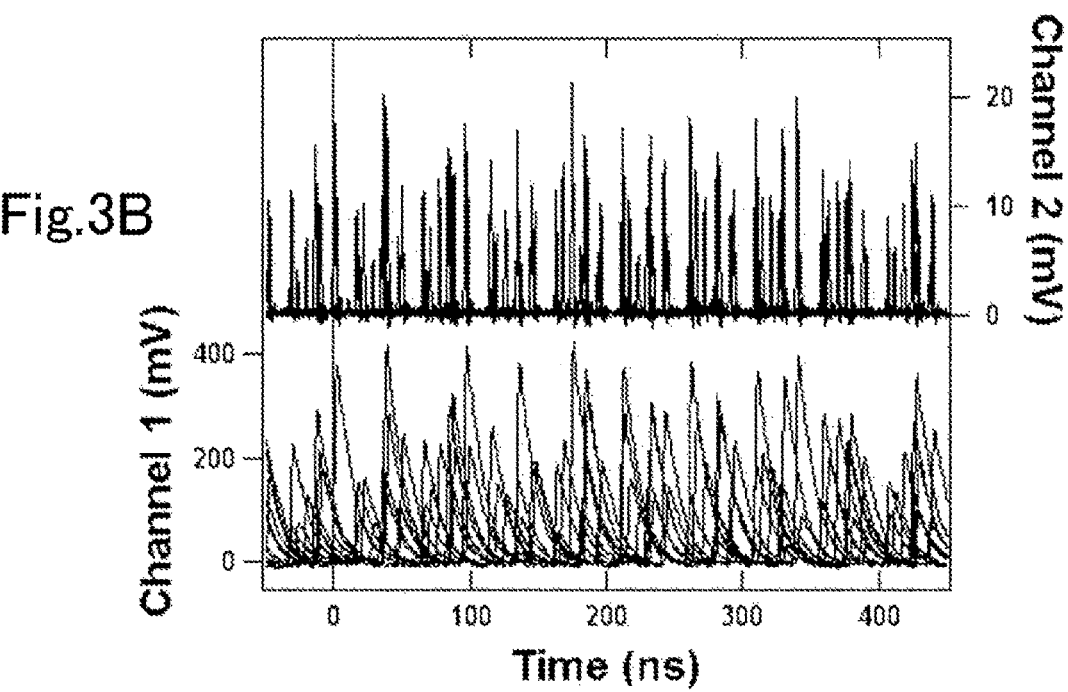

Fig.9A
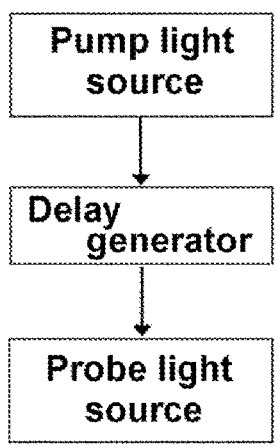
Fig.9B
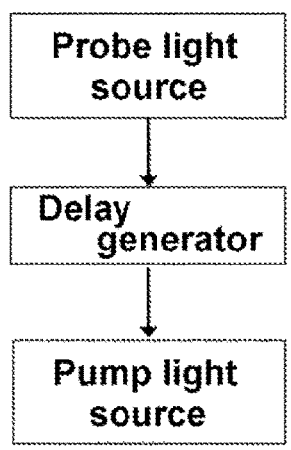
Fig.9C
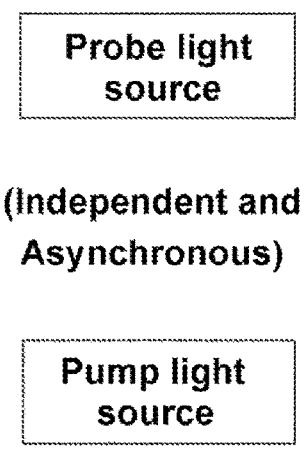
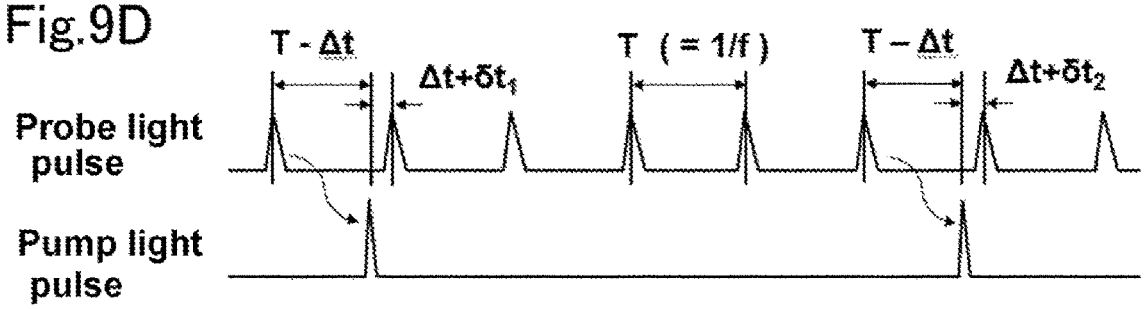

TRANSIENT ABSORPTION MEASUREMENT METHOD AND TRANSIENT ABSORPTION MEASUREMENT APPARATUS

TECHNICAL FIELD

Present invention relates to a transient absorption measurement method and a transient absorption measurement apparatus that use pump light and probe light.

BACKGROUND ART

Transient absorption measurement, which is also called Flash photolysis, is a method to observe change in absorption of monitor light (called probe light) caused in a sample in a short time scale after irradiation of pulsed light (called pump light) on the sample which induces excitation and photoreaction in the sample material. There are two major methods: one is a CW (continuous-light) probe method which is used in a slower timescale, and the other is a pump-probe method which is used in a pico-and femtosecond time region.

The CW probe method uses continuous wave light or flash lamp light having relatively long light emission time as probe light (see, for example, Patent Document 1). Under the CW probe method, response time or temporal gate width that a detector has, determines a limitation to time resolution. Typically, time resolution of about 10-50 nanoseconds is the limitation in the CW probe method. Since a shorter time region than this region is a so-called high frequency range in a GHz band, there has been a problem that it is difficult to obtain an accurate transient absorption signal free from distortion.

On the other hand, pulse light is used for probe light in the pump-probe method. Specifically, a pulsed light beam with a pulse width of picosecond or less emitted from a single light source is divided into two beams. One of the two beams irradiates the sample as pump light and induces photochemical reaction in the sample. The other one passes through the sample as probe light after being delayed by an optical delay stage. Delay time between the pump light and the probe light is provided in a desired length. Hence, time-resolved transient absorption data can be obtained by scanning the delay time.

Under the pump-probe method, information only at one moment in the rapid reaction, i.e. in time width corresponding to the pulse width, after the pump light irradiation can be captured even by a relatively slow detector because pulse light is used as probe light. The obtained information has time resolution corresponding to pulse width of probe light, and hence, if the pulse width is femtosecond, the time resolution will also be femtosecond. However, the delay time of the probe light pulse from the pump light pulse practically has an upper limit because the delay time is generated by a mechanical delay stage. Specifically, it is difficult to use 1.5 meter or longer delay stages which corresponds to 5 nanoseconds based on speed of light. Accordingly, the pump-probe method has an upper time limit and is not suitable for the measurement in the time region longer than 5 nanoseconds.

The performance that is demanded in a recent transient absorption method is measurement capability in a time region from 100 picosecond to 1 millisecond covering 5 to 50 nanoseconds where either CW probe methods or pump probe methods are not suitable to be used ("gap region" in conventional transient absorption measurements). One of methods that realize those measurements is use of a streak camera in a CW probe method (see, for example, Patent Document 2). However, a streak camera is an exceptionally expensive detector, and also has a problem that one model cannot cover a wide time range. Several methods have been proposed in which delay time up to millisecond is generated actively and electrically by probe light synchronizing with pump light (see, for example, Non-patent Documents 1, 2). However, any of them has a problem that measurement in a wide time-domain requires very long time since only a single probe light pulse is used for a single pump light pulse.

PRIOR ART DOCUMENTS

Patent Documents

Patent Document 1: Japanese Patent Laid-open Publication No. 2007-212145
Patent Document 2: Japanese Patent Laid-open Publication No. 2003-35665

Non-patent Documents

Non-patent Document 1: Rev. Sci. Instrum. 80, 026102 (2009)
[Non-patent Document 2: Rev. Sci. Instrum. 84, 073107 (2013)

SUMMARY OF THE INVENTION

Problems to be Solved by the Invention

The present invention is achieved in consideration of the above problems, and an object thereof is to provide a transient absorption measurement method and a transient absorption measurement apparatus which enable, with a simple structure, measurement of transient absorption over a wide time region including a gap region of conventional techniques, and enable, in a short time, measurement of transient absorption at a large number of sampling times.

Solutions to the Problems

In order to solve the above problems and to achieve the above object, a transient absorption measurement method according to a first aspect of the present invention comprises following acts (a) to (c).

(a) by use of: a pump light source for repeatedly generating a pump light pulse; and a probe light source for repeatedly generating a probe light pulse in a shorter repetition time interval than the pump light pulse, the probe light pulse having a delay time with respect to the pump light pulse shifting every time the pump light pulse is generated, repeatedly irradiating the pump light pulse on a sample, and repeatedly irradiating the probe light pulse on the sample every time the pump pulse is irradiated;

(b) detecting an intensity of a probe light pulse having passed through the sample; and (c) by measuring, every time the pump light pulse is irradiated, a shift in a delay time of the probe light pulse with respect to the pump light pulse occurring every time the pump light pulse is generated, obtaining transient absorption measurement data of the sample based on detected data of the probe light pulse intensity obtained in higher time density than time density of repetition of the probe light pulse.

With this configuration, the detected data of the intensities of the probe light pulses are obtained over a time region longer than the repetition time interval of the probe light pulse (which is a period if being constant) and, at the longest, corresponding to the repetition time interval of the pump light pulse and in higher time density than the time density of repetition of the probe light pulse (which is a frequency if being constant), and the transient absorption measurement data of the sample is obtained based on the detected data. Thus, the transient absorption measurement data is obtained in higher time density than the repetition time interval of the pump light pulse and also than the repetition time interval of the probe light pulse in a short time.

Further, since the probe light pulse is employed in this method contrary to the CW (continuous-light) probe method, time resolution corresponding to the pulse width of the probe light pulse is realized similarly to the conventional pump-probe methods. In addition, since the probe light pulse is repeatedly generated within a repetition time interval of the pump light pulse contrary to the conventional pump-probe method, and the delay time of the probe light pulse shifts every time the pump light pulse is generated, a time region of measurement can be expanded depending on the repetition time interval of the pump light pulse while maintaining a required time density of the transient absorption data. Thus, the transient absorption measurement can be performed over a wide time region including the gap region in the conventional technique.

No particularly expensive and complicated device is required to generate the probe light pulse having a delay time with respect to the pump light pulse shifting every time the pump light pulse is generated. In addition, it is also possible to employ a pump light source and a probe light source independent of each other, which generate the pump light pulse and the probe light pulse in a manner asynchronous with each other. The asynchronism will not require even a mechanism for adjusting timings when the pump and probe light sources generate pulses to each other.

A transient absorption measurement method according to a second aspect of the present invention is the transient absorption measurement method according to the first aspect, wherein the detection of an intensity of a probe light pulse having passed through the sample is performed by use of a light intensity detector for detecting intensity of light. The transient absorption measurement method further comprises detecting a background light intensity which is a light intensity detected by the light intensity detector at a time shifted from a time when the probe light pulse is detected. Further, the transient absorption measurement data is obtained through correction that subtracts, from the detected data of the probe light pulse intensity, a detected data of the background light intensity at a corresponding time.

With this configuration, the background light intensity, since being detected at a time shifted from the time when the probe light pulse is detected, corresponds to a light intensity detected by the light intensity detector when the probe light is not made incident. Accordingly, as the background light intensity, an intensity of concomitantly emitted light, such as scattered light, fluorescence, phosphorescence and the like, which the sample concomitantly in some case emits within a short period after the pump light pulse is irradiated on the sample, is detected. A true probe light pulse intensity free from an influence of the concomitantly emitted light is obtained by subtracting, from the detected probe light pulse intensity, the background light intensity at a corresponding time. Based thereon, the transient absorption measurement data is obtained. Thus, with this configuration, the transient absorption measurement data free from an influence of the concomitant light emission is obtained. Conventional measurements, to remove the intensity of the concomitant light emission from the data of the probe light pulse intensity, require an additional measurement to measure only an intensity of the concomitantly emitted light while blocking the probe light by use of "a shutter," "an optical chopper" and the like. With this configuration, the transient absorption measurement data free from an influence of the concomitant light emission is obtained in a short time without the additional measurement but with a simple configuration.

A transient absorption measurement method according to a third aspect of the present invention is the transient absorption measurement method according to the first or second aspect, wherein the pump light source and the probe light source are independent of each other and generate the pump light pulse and the probe light pulse in a manner asynchronous with each other.

With this configuration, the pump light pulse and the probe light pulse having a delay time with respect to the pump light pulse shifting every time the pump light pulse is generated can repeatedly be generated with a simple configuration without a mechanism for adjusting timings when the pump light source and the probe light source generates pulses to each other. Following should be noted. The term "light sources being independent" means respective light sources generate light individually without light generated by one light source being split for example and utilized as light generated by the other light source. The term "pulses being asynchronous" means that pulses are not synchronized; in other words, respective timings when the pulses are generated are not adjusted to each other.

A transient absorption measurement apparatus according to a fourth aspect of the present invention comprises a pump light source, a probe light source, a light introduction path, a pump light pulse detector, a probe light pulse detector, and a probe light intensity recorder. The pump light source is for repeatedly generating a pump light pulse. The probe light source is for repeatedly generating a probe light pulse in a shorter repetition time interval than the pump light pulse, the probe light pulse having a delay time with respect to the pump light pulse shifting every time the pump light pulse is generated to thereby repeatedly generate the probe light pulse every time the pump light pulse is generated. The light introduction path is for introducing the pump light pulse generated by the pump light source and the probe light pulse generated by the probe light source to a sample. The pump light pulse detector is for detecting the pump light pulse. The probe light pulse detector is for detecting the probe light pulse, the probe light pulse detector including a probe light intensity detector for detecting an intensity of the probe light pulse having passed through the sample. The probe light intensity recorder is for recording, every time the pump light pulse is detected by the pump light pulse detector, each of intensities of a train of probe light pulses detected by the probe light intensity detector within a certain period crossing an origin time which is a time when the pump pulse is detected, in association with a corresponding one of probe light pulse time data which express times when the probe light pulse detector detects the train of probe light pulses with the origin time as a basis.

With this configuration, since the repetition time interval of the probe light pulse (which is a period if being constant) is shorter than that of the pump light pulse, and the probe light pulse is repeatedly generated every time one pump light pulse is generated, the probe light intensity recorder records intensities of a train of probe light pulses over a certain period crossing the origin time every time when one pump light pulse is detected. Further, since the delay time of the probe light pulse with respect to the pump light pulse shifts every time the pump light pulse is generated, the detected intensity of the probe light pulse is accumulated in the probe light intensity recorder over the certain period crossing the origin time in a finer time interval than the repetition time interval of the probe light pulse by repeatedly recording the intensities of the train of probe light pulses and corresponding time data every time the pump light pulse is detected. Simply extending recording time so as to increase the number of detections of the pump light pulse advantageously results in increase in fineness of the time interval. Since, in the probe light intensity recorder, the probe light pulse intensities are recorded in association with the probe light pulse time data, the transient absorption measurement data, such as a transient absorption curve, can be obtained based on those recorded data. Thus, the transient absorption measurement data can be obtained in a short time and in a higher time density than the frequency of the pump light pulse and also than the frequency of the probe light pulse. Further, for a reason similar to that stated on the first aspect of the present invention, the transient absorption can be measured within a wide time region including the gap region in the conventional technique, and the transient absorption measurement data can be obtained in a required time density even for a measurement within a longer time region. In addition, as stated on the first aspect of the present invention, no particularly expensive and complicated device is required to generate the probe light pulse having a delay time with respect to the pump light pulse shifting every time the pump light pulse is generated.

Following should be noted. The term "time data expressing time" is not restricted to data directly expressing time but includes data associated with time and capable of deriving time, i.e., data indirectly expressing time. Recording intensities of a train of probe light pulses in response to the detection of the pump light pulse as a trigger by use of an oscilloscope as the probe light intensity recorder is nothing but one example of recording the intensities of a train of probe light pulses with the origin time as a basis in association with the probe light pulse time data.

A transient absorption measurement apparatus according to a fifth aspect of the present invention is the transient absorption measurement apparatus according to the fourth aspect, wherein the probe light source generates the probe light pulse at a constant frequency. The probe light pulse detector includes a high-speed probe light pulse detector for detecting the probe light pulse with higher time accuracy than the probe light intensity detector. The pump light pulse detector is a high-speed pump light pulse detector for detecting the pump light pulse with higher time accuracy than the probe light intensity detector. The probe light intensity recorder includes a delay time measurement device for measuring, in response to detection of the pump light pulse by the high-speed pump light pulse detector as a trigger, a period until the high-speed probe light pulse detector, thereafter, firstly detects the probe light pulse. The probe light pulse time data include the period measured by the delay time measurement device and an order in which the probe light detector detects the train of probe light pulses.

With this configuration, on condition that the frequency of the probe light pulse is known by, for example, having been measured in advance, the detection times when the train of probe light pulses are detected with the origin time as a basis can be specified with higher time precision than the time precision of the probe light intensity detector based on the period measured by the delay time measurement device and the order in which the probe light detector has detected the train of probe light pulses, both of which are recorded in the probe light intensity recorder. Thus, the transient absorption measurement data can be acquired with higher time precision than the time precision of the probe light intensity detector based on the frequency of the probe light pulse and the data recorded by the probe light intensity recorder.

A transient absorption measurement apparatus according to a sixth aspect of the present invention is the transient absorption measurement apparatus according to the fourth or fifth aspect, wherein the probe light intensity recorder further records a background light intensity detected by the probe light intensity detector at a time shifted from a time when the probe light pulse is detected within at least an initial certain period on and after the origin time for each pump light pulse, in association with a background light detection time data which expresses the shifted time with the origin time as a basis.

With this configuration, the background light intensity, as well as the probe light pulse intensity, is accumulated in the probe light intensity recorder within at least an initial certain period on and after the origin time in a finer time interval than the repetition time interval of the probe light pulse. The background light intensity, since being detected at a time shifted from the time when the probe light pulse is detected, corresponds to a light intensity detected by the probe light intensity detector when the probe light is not made incident. Accordingly, as the background light intensity, an intensity of concomitantly emitted light, such as scattered light, fluorescence, phosphorescence and the like, which the sample concomitantly in some case emits within a short period after the pump light pulse is irradiated on the sample, is recorded. A true probe light pulse intensity free from an influence of the concomitantly emitted light is obtained by subtracting, from the detected and recorded probe light pulse intensity, the background light intensity at a corresponding time. Thus, with this configuration, the intensity of the concomitant light emission is recorded in the same time density as the probe light pulse intensity is, and thereby, the transient absorption measurement data excluding an influence of the concomitant light emission with a high precision can be obtained. Further, for a reason similar to that stated on the second aspect of the present invention, the data of the concomitant light emission intensity can be obtained together with the data of the probe light pulse intensity in a short time with a simple configuration but without the measurement that is required in the conventional method and is performed while blocking the probe light, and the data of the concomitant light emission intensity superimposed on the data of the probe light pulse intensity can be removed.

A transient absorption measurement apparatus according to a seventh aspect of the present invention is the transient absorption measurement apparatus according to the sixth aspect, further comprising an image data generator for, based on (i) the intensities of the train of probe light pulses and the probe light pulse time data for each pump light pulse recorded by the probe light intensity recorder in a manner of association and (ii) the background light intensities within the at least initial certain period and the background light detection time data for each pump light pulse recorded by the probe light intensity recorder in a manner of association, generating image data expressing differences, ratios or logarithms of ratios between the corrected intensities of the train of probe light pulses obtained by subtracting, from each of the intensities of the train of probe light pulses for each pump light pulse, the background light intensity at a corresponding time and the intensity of the probe light pulse preceding the origin time as temporal change on a coordinate system having a time axis and a data axis crossing the time axis.

With this configuration, the image data expressing, as temporal change, differences, ratios or logarithms of ratios between the corrected intensities of the train of probe light pulses and the intensity of the probe light pulse preceding the origin time, i.e., image data expressing the transient absorption free from an influence of the concomitant light emission is generated by the image data generator. The image data expresses the transient absorption by a set of points, or a polygonal line or a smooth curve connecting a set of points, for example. The generated image data can be recorded in a memory device, displayed on a display screen, or printed out by a printer or the like, for example. For the coordinate system, various types, such as linear, semilogarithmic, logarithmic ones, can be employed.

A transient absorption measurement apparatus according to an eighth aspect of the present invention is the transient absorption measurement apparatus according to any of the fourth to sixth aspects, further comprising a reference probe light intensity detector for detecting, as a reference probe light pulse intensity, an intensity of the probe light pulse before passing through the sample. The probe light intensity recorder further records, together with each of the intensities of the train of probe light pulses detected by the probe light intensity detector, a corresponding reference probe light pulse intensity detected by the reference probe light intensity detector in association with a corresponding one of the probe light pulse time data.

With this configuration, the probe light pulse intensity recorded in the probe light intensity recorder can be corrected by the reference probe light intensity at a corresponding time, and thereby, the probe light pulse intensity free from an influence of fluctuation in the intensity of the probe light pulse incident on the sample can be obtained. Thus, the transient absorption measurement data free from an influence of the intensity fluctuation of the probe light pulse incident on the sample can be obtained.

A transient absorption measurement apparatus according to a ninth aspect of the present invention is the transient absorption measurement apparatus according to the eighth aspect, further comprising an image data generator. The image data generator is for, based on the intensities of the train of probe light pulses, the reference probe light pulse intensity and the probe light pulse time data for each pump light pulse recorded by the probe light intensity recorder in a manner of association, generating image data expressing differences, ratios or logarithms of ratios between (i) corrected intensities obtained by correcting each of the intensities of the train of probe light pulses for each pump light pulse by a corresponding reference probe light pulse intensity and (ii) a corrected intensity obtained by correcting the intensity of the probe light pulse proceeding the origin time by a corresponding reference probe light pulse intensity as temporal change on a coordinate system having a time axis and a data axis crossing the time axis.

With this configuration, by the image data generator, image data expressing the transient absorption free from an influence of intensity fluctuation of the probe light pulse incident on the sample is generated. Examples of the image data and the coordinate system are as stated above.

A transient absorption measurement apparatus according to a tenth aspect of the present invention is the transient absorption measurement apparatus according to the fourth or fifth aspect, further comprising an image data generator. The image data generator is for generating image data expressing differences, ratios or logarithms of ratios between intensities of a train of probe light pulses and an intensity of a probe light pulse preceding the origin time for each pump light pulse as temporal change on a coordinate system having a time axis and a data axis crossing the time axis based on intensities of the train of probe light pulses and the probe light pulse time data for each pump light pulse recorded by the probe light intensity recorder in a manner of association.

With this configuration, image data expressing the transient absorption is generated by the image data generator. Examples of the image data and the coordinate system are as stated above.

A transient absorption measurement apparatus according to an eleventh aspect of the present invention is the transient absorption measurement apparatus according to any of the fourth to tenth aspects, wherein the pump light source and the probe light source are independent of each other and generate the pump light pulse and the probe light pulse in a manner asynchronous with each other.

With this configuration, the pump light pulse and the probe light pulse having a delay time with respect to the pump light pulse shifting every time the pump light pulse is generated can repeatedly be generated with a simple configuration without a mechanism for adjusting timings when the pump light source and the probe light source generates pulses to each other. The meanings of the terms "light sources being independent" and "pulses being asynchronous" are as stated above.

Effects of the Invention

According to the present invention as described above, a transient absorption measurement method and a transient absorption measurement apparatus which enable, with a simple structure, measurement of transient absorption over a wide time region including a gap region in conventional techniques, and enable, in a short time, measurement of transient absorption at a large number of sampling times are obtained.

The objects, characteristics, features, and advantages of the present invention will be elucidated by the following detailed description and the attached drawings.

BRIEF DESCRIPTION OF THE DRAWINGS

FIGS. 2A to 2D are drawings illustrating the operation of the transient absorption measurement apparatus of FIG. 1.

FIGS. 3A and 3B are graphs showing waveforms measured by an oscilloscope in a verification experiment.

FIGS. 9A to 9D are drawings showing exemplary configurations of a probe light source and a pump light source according to still other embodiments of the present invention.

EMBODIMENTS OF THE INVENTION

1. Configuration and Function of an Apparatus

Figure 1:
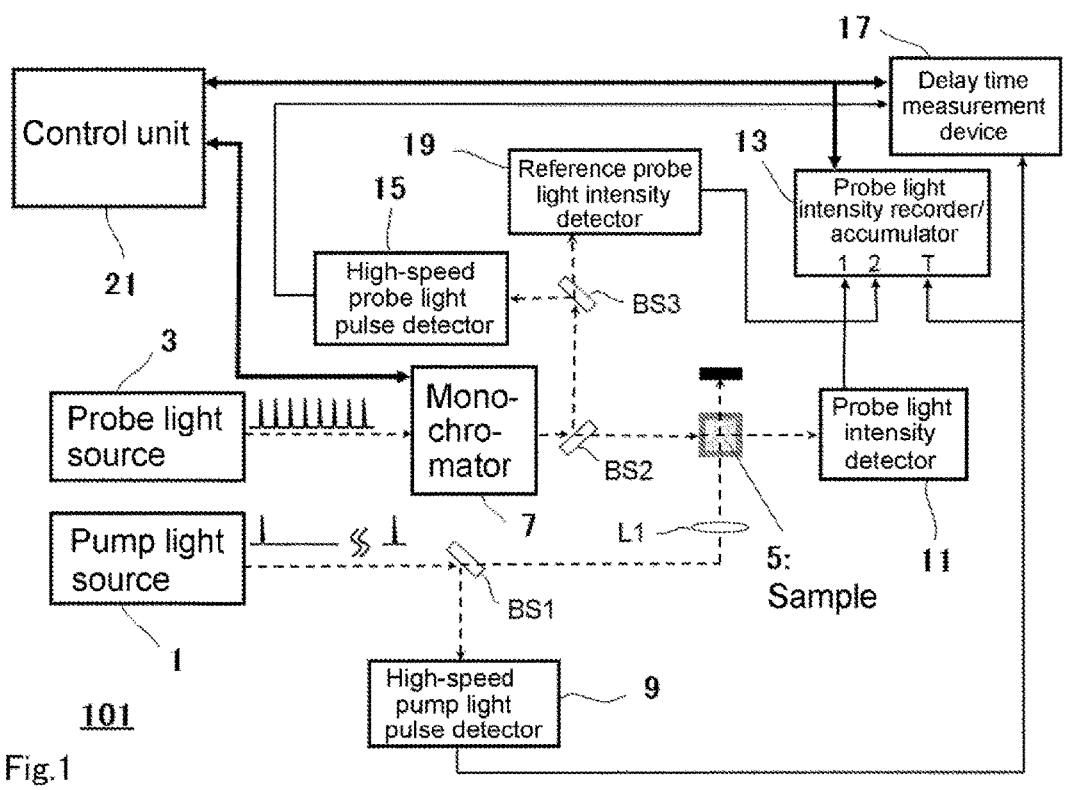
FIG. 1 is a block diagram illustrating a configuration of a transient absorption measurement apparatus according to one embodiment of the present invention.

FIG. 1 is a block diagram illustrating a configuration of a transient absorption measurement apparatus according to one embodiment of the present invention. This apparatus 101 has a pump light source 1, a probe light source 3, a monochromator 7, a high-speed pump light pulse detector 9, a probe light intensity detector 11, a probe light intensity recorder/accumulator 13, a high-speed probe light pulse detector 15, a delay time measurement device 17, a reference probe light pulse intensity detector 19 and a control/analysis apparatus 21. When the instrument 101 is used, a sample 5 is held at a sample holder (not shown in the figure). The optical path from the pump light source 1 to the sample 5 and the path from the probe light source 3 to the sample 5 correspond to one of examples of the light introduction path of the present invention. The probe light intensity detector 11 corresponds to one example of the probe light intensity detector of the present invention. The probe light intensity detector 11 and the high-speed probe light pulse detector 15 constitute one example of the probe light detector of the present invention. The probe light intensity recorder/accumulator 13 and the delay time measurement device 17 constitute one of the probe light intensity recorder of the present invention. The control/analysis apparatus 21 corresponds to one example of the image data generator of the present invention. The reference light pulse intensity detector 19 corresponds to one example of the reference probe light intensity detector of the present invention.

The pump light source 1 is, for example, a laser light source with a pulse width of 100 ps and a repetition rate of 1 kHz. The probe light source 3 is independent of and asynchronous with the pump light source 1, is far higher in repetition rate than the pump light source 1, and is, for example, a broadband (white-light) super continuum light source with a pulse width of 10 ps and a repetition rate of 20 MHz. The pump light is split into two beams before passing through the sample 5 by a beam splitter BS1. One of the beams split into is detected by the high-speed pump light pulse detector 9 (bandwidth>500 MHz). The output of the detector 9 is inputted to the delay time measurement device 17 and is used as a start signal for delay time measurement, and at the same time, it is used as a start signal for the probe light intensity recorder/accumulator 13. The other beam intersects with probe light in the sample.

Probe light is monochromatized by going through the monochromator 7, and split into two beams by the beam splitter BS2 before passing through the sample 5. One of the beams split into intersects with the pump light in the sample 5, thereafter enters the probe light intensity detector 11 (bandwidth>14.6 MHz, to be explained below). The output of the detector 11 enters a channel 1 of the probe light intensity recorder/accumulator 13. The other beam is further split into two beams by another beam splitter BS3. One of the beams secondly spitted into is detected by the high-speed probe light pulse detector 15 (bandwidth>500 MHz), and the output of the detector 15 enters the delay time measurement device 17 and is used for the end signal of the time delay measurement. The other one of the beams secondly split into is detected by the reference probe light intensity detector 19 (bandwidth>14.6 MHz), and the output of the detector 19 is inputted to a channel 2 of the probe light intensity recorder/accumulator 13.

FIGS. 2A to 2D illustrate the operation of the transient absorption measurement apparatus 101. The delay time measurement device 17 measures time difference $\Delta t$ between the rising edge of a signal outputted from the high-speed pump light pulse detector 9 and the rising edge of a signal outputted from the high-speed probe light pulse detector 15, and records the time difference. The probe light intensity recorder/accumulator 13, being triggered by the rising edge of a signal outputted from the high-speed pump light pulse detector 9, records intensities of pulses which are n in total number immediately before, at and after the triggering, such as individual peak voltage values or integral values of pulses for each of the reference probe light intensity detector 19 and the probe light intensity detector 11. Delay times t with respect to the pump light regarding n pulses that were recorded in the memory stated above are given by the following Formula 1 with a repetition rate of the probe light pulses referred to as f, $$t=\Delta t-1/f, \Delta t, \Delta t+1/f, \Delta t+2/f, \Delta t+3/f, \Delta t+4/f, \ldots, \Delta t+(n-1)/f \ldots \quad (1)$$

Here, the initial delay, $\Delta t-1/f$, is a delay time of the pulse immediately before the trigger, and has negative value. For these time delays, by referring to the signal obtained from the probe light intensity detector 11 as I_sam(t), and to the signal obtained from the reference probe light intensity detector 19 as I_ref(t), the transient absorption data $\Delta OD(t)$ can be calculated by following Formula 2 as logarithm of ratio of light intensity after the irradiation of the pump light to the one before the irradiation of pump light (that is, at $t=\Delta t-1/f$).

$$\Delta OD(t)=\log[\{I\_sam(\Delta t-1/f)/I\_ref(\Delta t-1/f)\}/\{I\_sam(t)/I\_ref(t)\}] \ldots \quad (2)$$

If the stability of the probe light source 3 is good enough (that is, I_ref(t) ≈ I_ref($\Delta t-1/f$)), the transient absorption data $\Delta OD(t)$ does not have to be corrected by the output of the reference probe light intensity detector 19, and can be calculated by following Formula 3.

$$\Delta OD(t)=\log[\{I\_sam(\Delta t-1/f)/I\_sam(t)\}] \ldots \quad (3)$$

As a result of the above, transient absorption signals of the sample 5 regarding n sampling points can be measured with one pump light irradiation. Since probe light and pump light are generated independently and asynchronously, different $\Delta t$ in $0<\Delta t<1/f$ can be obtained every time when the pump light is irradiated, and hence, many times of pump light irradiation cause the time segment of 0 to 1/f to be filled with dense $\Delta t$. Consequently, a reaction curve (transient absorption curve) can be reconstructed in the time region indicated by the following Formula 4 with the time resolution of the delay time measurement device (see FIG. 2D).

$$-1/f \sim 0 \sim 1/f \sim 2/f \sim \ldots \sim (n-1)/f \ldots \quad (4)$$

For example, when f=20 MHz and n=10000, a transient absorption curve in the time range of −50 ns to 499950 ns (=499.95 μs) can be obtained. Time resolution almost corresponds to the square root of the summation of squares of pulse width of the pump light, pulse width of the probe light and accuracy of delay time measurement. Therefore, if the pulse width of the light source(s) 1, 3 are long enough than the accuracy of the delay time measurement device 17, time resolution will be determined by the pulse width of light source(s) 1, 3. To the contrary, if pulse width of light source(s) 1, 3 is sufficiently short, time resolution will depend on the accuracy of the delay time measurement device 17. The accuracy of the time delay measurement can be ⅕ of a time constant τ=1/(2πBs) of two high speed pulse detectors 9 and 15 with a bandwidth of Bs by using known technology like a pulse height discrimination circuit. For example, when Bs is 1 GHz, the time resolution shown by following Formula 5 can be realized. Here, symbol "*" indicates multiplication.

$$1/(2\pi*1*10^9)*(1/5)s = 33 \text{ ps} \ldots \quad (5)$$

Bandwidths Br of the probe light intensity detector 11 and the reference probe light intensity detector 19 are the values which enable probe pulses having repetition frequency of f(Hz) to be measured precisely and separately. The shapes of signals outputted from the detectors are determined by bandwidth and follow the expression $y(t)=A*\exp\{-t*2\pi Br\}$. Hence, from the condition that an amplitude should be 1% or less when a next pulse comes, i.e., $y(t=1/f)<0.01*A$, the bandwidth Br is determined by the following Formula 6.

$$y(1/f)=A*\exp\{-(1/f)*2\pi Br\}<0.01*A; Br > -\ln(0.01)*f/2\pi = 0.73*f \ldots \quad (6)$$

For example, when the frequency of the probe light f is f=20 MHz, Br>0.73*20*10^6 Hz=14.6 MHz, and hence, it is understood that bandwidth more than 14.6 MHz is desirable. However, since high-frequency noise increases with an increase in the bandwidth, unnecessarily high Br is undesirable.

2. Verification Experiment

Next, there will be explained the procedure and result of experiment performed to verify effectivity of the present invention. In the verification experiment, PowerChip PNV-001525-100, TEEM PHOTONICS was employed for the pump light source 1. The repetition rate thereof was fixed at 1 kHz. Pulse width specified in its datasheet is 350 ps, and wavelength is 355 nm. This light is focused by a lens and impinged on the sample 5, and reflected light from this lens was entered into the high-speed pump light pulse detector 9.

Supercontinuum light source SC-450, Fianium, was used for the probe light source 3. Its repetition rate f is 20 MHz (in other words, repetition interval is 50 ns), seed light pulse width is 6 ps, and emission wavelength is from 450 nm to 2000 nm. White light from the SC-450 was previously monochromatized by a monochromator, MD-200, Unisoku, and thereafter split into 2 beams by a beam splitter; one beam was focused on the high-speed probe light pulse detector 15 while the other went through the sample 5 then was focused on the probe light intensity detector 11. The high-speed probe light pulse detector 15 was used also as the reference probe light intensity detector 19.

The two high-speed pulse detectors 9, 15 are non-amplified silicon photodiodes S5973, HAMAMATSU, and their bandwidths Bs are 1 GHz. For the probe light intensity detector 11, a PIN-photodiode S1722-02, HAMAMATSU, with an amplifier (bandwidth Br=20 MHz), Unisoku, was used.

For the probe light intensity recorder/accumulator 13, an oscilloscope HDO-4022, Lecroy, was employed. Its bandwidth is 200 MHz, rise time is 1.7 ns, a maximum sampling rate is 2.5 GS/s, trigger and interpolator jitter is 4.5 ps. The oscilloscope is equipped with a sequence mode to record each triggered event separately. The oscilloscope has a sampling interval of 400 ps at the maximum, whereas has a function of recording the rising timing of the first internal clock for each trigger with the accuracy of 10 ps or shorter with respect to the rising edge of the signal inputted into a trigger channel. This function can be used as a substitute for the delay time measurement device 17.

Outputs of the two detectors, the probe light intensity detector 11 and the high-speed probe light pulse detector 15 were inputted into channels 1 and 2 of the oscilloscope, respectively. The output of the high-speed pump light pulse detector 9 was inputted into an Ext channel of the oscilloscope and was used as a trigger. The full scale of the oscilloscope was set at 2000 ns=2 μs so that 40 probe pulses (repetition interval is 50 ns) can be recorded. 2500 events each including those 40 pulses were recorded for maximum 2500 trigger signals.

FIGS. 3A and 3B are graphs that show waveforms measured by the oscilloscope, and the horizontal axes show time, the lower vertical axes show input voltage for channel 1, and the upper vertical axes show input voltage for channel 2. FIG. 3A shows waveforms for a single trigger (only first 10 pulses are shown) and FIG. 3B shows waveforms for 10 triggers in an overlaid manner. As FIG. 3B shows, waveforms are recorded successively as if they bury gaps randomly because the probe pulse train is asynchronous with the pump light. As supercontinuum light source, SC-450, that was used for the verification experiment was accidentally unstable, so that the light intensity of each pulse largely fluctuated as seen in FIGS. 3A and 3B. However, it is possible to make the light intensity of each pulse almost constant as shown in FIGS. 2A to 2D.

The sample 5 was acetonitrile solution of benzophenone. The sample 5 was prepared so that light absorbance at 355 nm became approximately 1, using an observation cell having the optical path length of 1 mm. Detection wavelength was set at 520 nm so that T-T absorption could be observed. In Benzophenone, intersystem crossing from an excited singlet state to a triplet state occurs very fast in such a short period as 30 ps or less, and the lifetime of the triplet state is about several hundred nanoseconds, and hence, the shape of transient absorption curve from 100 ps to several 10 nanoseconds can be considered to be almost an ideal step function. Based on the rise-up of the reconstructed transient absorption curve, time resolution of the verification system can be evaluated.

For an obtained waveform triggered by the pump pulse signal as shown in FIGS. 3A and 3B, the time when the signal on channel 2 reaches 50% of the peak value of each pulse waveform was calculated for 40 pulses and those times were regarded as Δt. As noted above, Δt can be obtained with the precision of 10 ps or shorter as the oscilloscope performance, and the rise timing of the pulse is also calculated with the precision of 33 ps or shorter as expressed in Formula 5. Each peak value of 40 pulses on the channel 2 is referred to as reference signal value, I_ref(Δt), and five sampling values at the vicinity of the peak position of a corresponding pulse on the channel 1 were averaged. The averaged value is referred to as a sample signal value I_sam(Δt). Then the fluctuation in pulse intensity was corrected for each of 40 pulses by calculating I_sam(Δt)/I_ref(Δt) (see Formula 2). These corrected pulse intensity values were allocated to the bin (section) of Δt with the width of 100 ps until 10 ns, 200 ps until 20 ns, 500 ps until 50 ns and 1 ns thereafter. This operation was repeated for many triggered events, and data entered in the same bin were averaged, then the averaged value was referred to as I(Δt) for the section.

Figure 4:
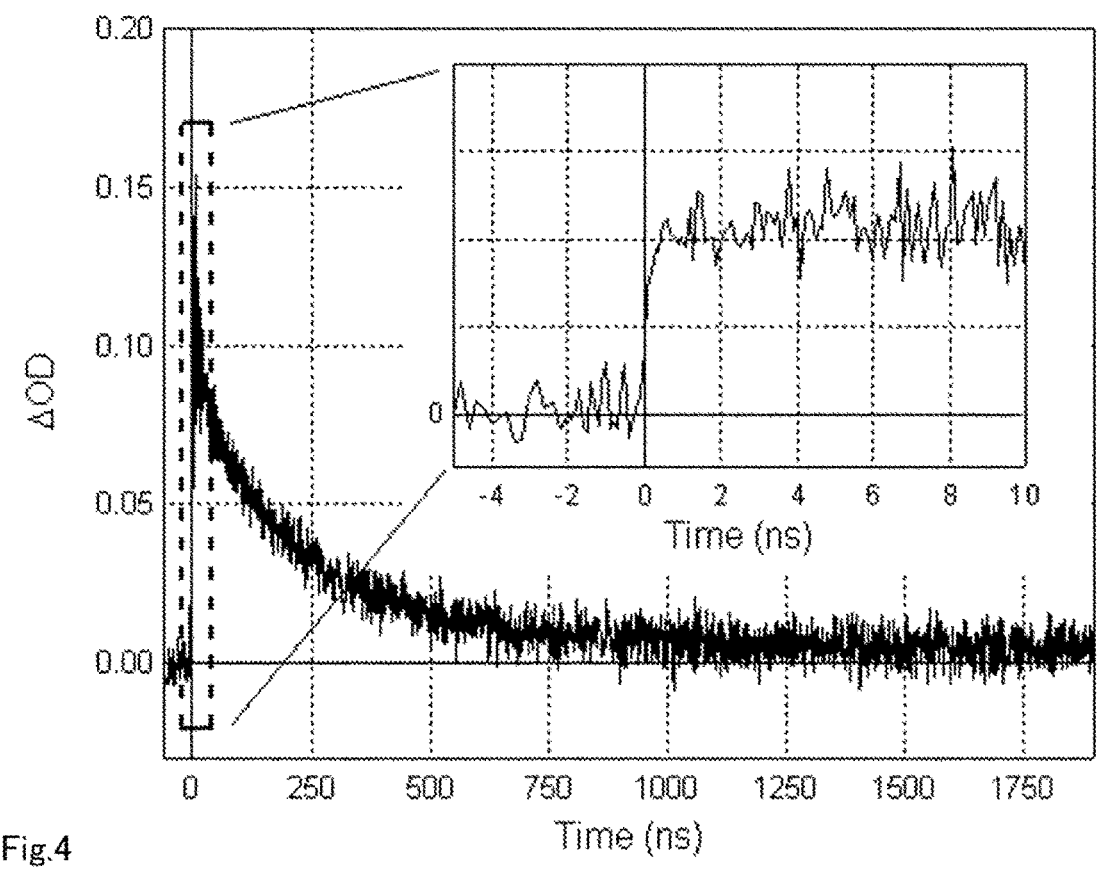
FIG. 4 is a graph showing a waveform reconstructed from the waveform measured by the oscilloscope in the verification experiment.

For the I(Δt) obtained in this way, ΔOD is calculated according to Formula 2, and a transient absorption curve was reconstructed. FIG. 4 is a graph that shows ΔOD(t) calculated from 2500 triggered events. Due to instability of the supercontinuum light source and usage of the high-speed probe light pulse detector 15 as a reference signal instead of the reference probe light intensity detector 19, signal to noise ratio was not good. Nevertheless, we can still see that high time resolution (see inset of FIG. 4, where time domain from −5 ns to 10 ns is expanded) and wide measurement time range corresponding to 40 pulses (50 ns*40=2000 ns=2 us) have been achieved at the same time.

Figure 5:
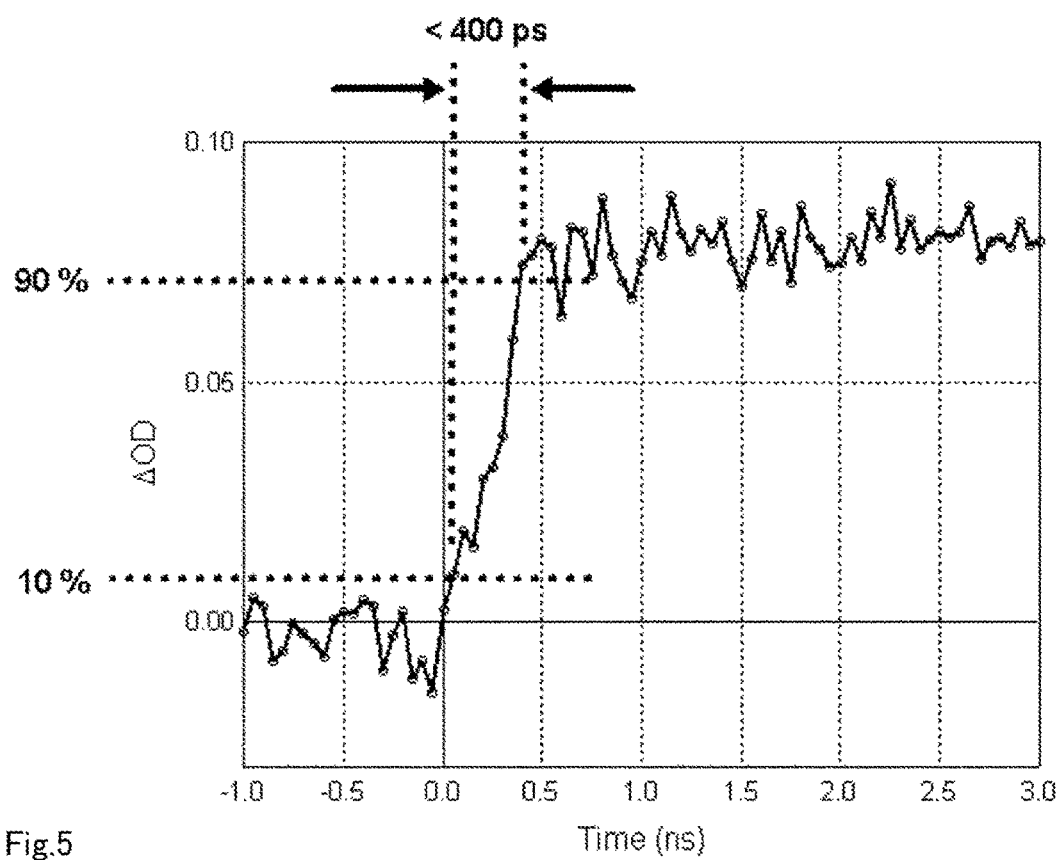
FIG. 5 is a graph showing a waveform reconstructed from the waveform measured by the oscilloscope in the verification experiment.

Next, to improve the accuracy of the experiment and evaluate the time resolution, measurement under the same condition was further repeated and the measured data were averaged. FIG. 5 is a graph that shows data reconstructed from 100,000 triggered events with the bin width set at 50 ps. Rise time of the signal (from 10% to 90%) was smaller than 400 ps. This value is close to the pulse width of the pump light, 350 ps, which is the largest value among accuracies of delay time measurement, and pulse widths of the pump light and probe light. It can be shown by numerical calculation that the rise time to be measured cannot be less than 350 ps*1.1=385 ps for the step-wise varying true transient absorption signal under the assumption of the shape of the pump light pulse being Gaussian. Accordingly, the time resolution obtained in FIG. 5 is said to be the best value that could be achieved in the constructed system. Therefore, it can also be said that the accuracy of delay time measurements was much better than 400 ps.

Since the bandwidth of the used oscilloscope is 200 MHz, the rise time calculated by (0.35/bandwidth) is 1.7 ns for the usual CW probe methods, and it is impossible to obtain better time resolution than that one. However, it can be said that, according to the system used for verification of the present invention, time resolution approximately 5 time better than that one was obtained. Although time resolution was limited by the pump light source with pulse width of 350 ps in the present verification system, better time resolution can be obtained by use of a pump light source with shorter pulse width.

Figure 6:
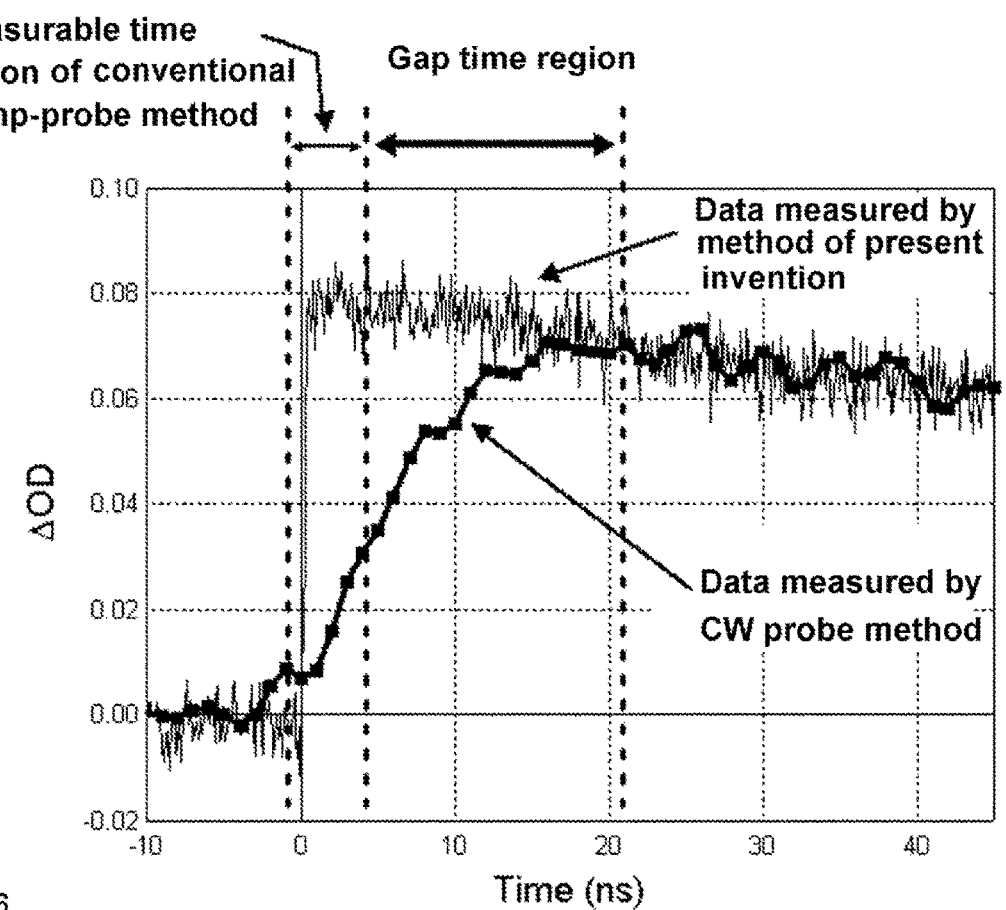
FIG. 6 is a graph showing results of the verification experiment and a conventional technique in a comparing manner.

In FIG. 6, data of the same sample 5 obtained by the commercial transient absorption system (TSP-1000, Unisoku, bandwidth 20 MHz, having the rise time of 16 ns) which uses a general CW method was overlaid to data measured by the present verification system. In FIG. 6, the time region where data can be acquired by using a general pump-probe method is also shown. The time domain where two waveforms do not overlap on the longer-time side of an unmeasurable domain of the pump-probe method is a gap time region (in this example, 5 ns-20 ns). Even according only to the verification data obtained by the verification system, the rise time is 40 times (=16 ns/400 ps) better in the verification system than in the commercial system, that is, the rise-up is extremely rapid. In addition, data was measured also in a long time range (5 ns or more) where data cannot be obtained by the conventional pump-probe method, which clearly shows the effectiveness of the present invention.

3. Another Embodiment (Removal of Emission Signal) and Verification Experiment Thereof For transient absorption measurements, a light scattering signal (Rayleigh scattering, Raman scattering), a fluorescence signal, and a phosphorescence signal caused by the pump light irradiation on the sample contaminate the signal of the probe light pulse intensity, and may cause problems. Hereinafter, any of these signals is called "an emission signal." The emission signal gives a false transient absorption signal that causes negative ΔOD in the fast time region, which often results in expansion of a gap time region especially in the CW probe method. To reduce the effects of the emission signal, in the conventional transient absorption measurements, only the emission signal is obtained by blocking the probe light, then the emission signal is subtracted from I_sam(t) before ΔOD is calculated by Formulas 2 and 3. However, the probe light intensity detector is often saturated by the emission signal since the probe light intensity is relatively weak compared to the emission signal in the CW probe methods. As a result, the subtraction is impossible in many cases in fact.

On the other hand, in the present invention, the emission signal can be removed from a set of raw data including emission signal without blocking the probe light by a shutter, optical chopper or the like. Since the present invention uses the probe light pulse relatively large in intensity compared to the emission signal, the amplification gain of a detector can be set low. As a result, an emission signal can precisely be obtained without the detector saturated, and the subtraction procedure can correctly be performed. By using the above-described verification system, precise extraction and almost complete removal of the emission signal were verified. Hereinafter, the process and result of the emission signal removal by using the verification system is explained with reference to graphs shown in FIGS. 7A to 7D.

Figure 7:
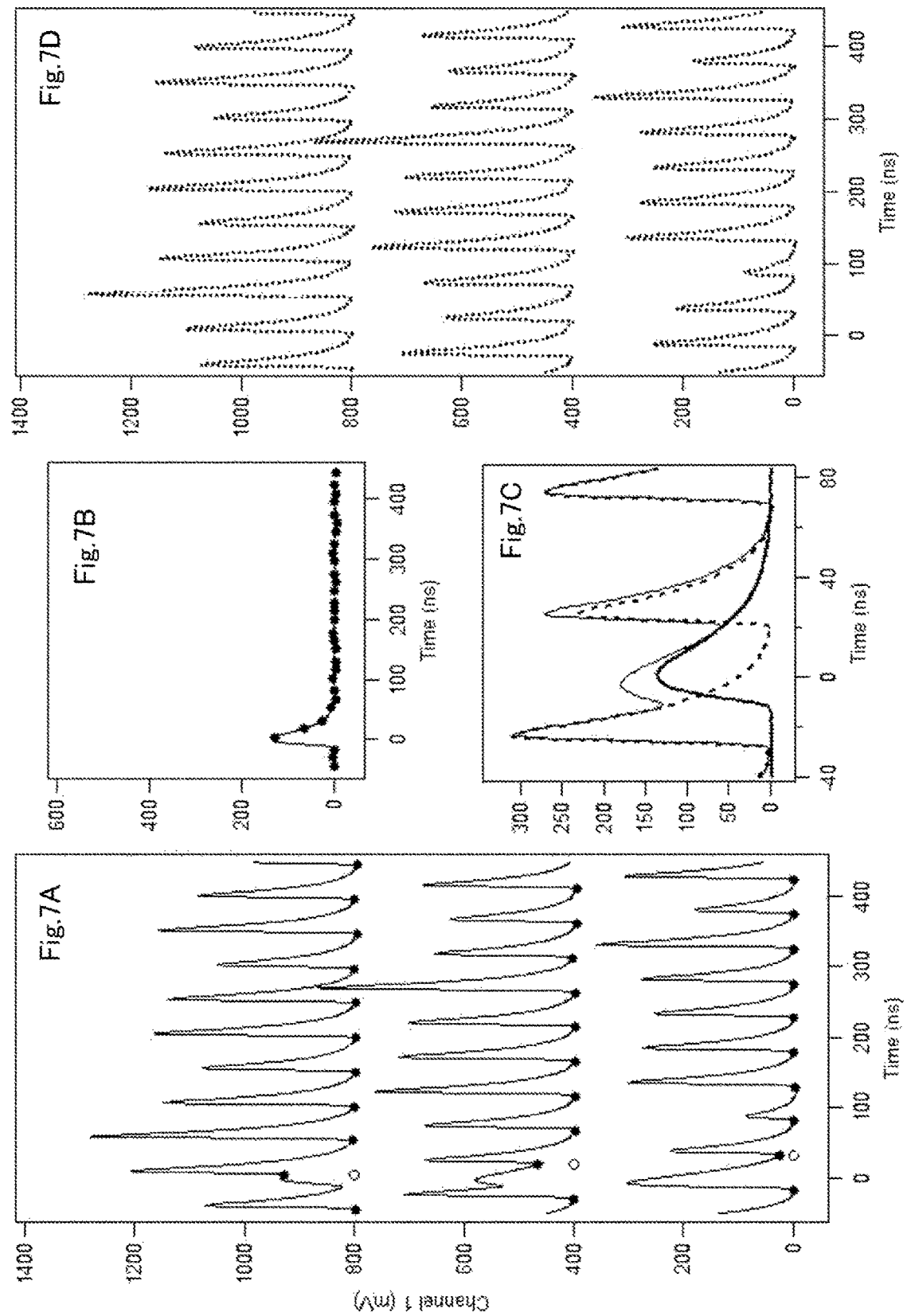
FIGS. 7A to 7D are graphs showing waveforms measured by an oscilloscope in a verification experiment on a transient absorption measurement apparatus according to another embodiment of the present invention.

FIG. 7A shows raw data obtained for three triggered events with an intense fluorescent sample (tetraphenylporphyrin in acetone, hereinafter referred to as TPP) by the probe light intensity detector 11. The horizontal axis indicates time, and the vertical axis indicates the intensity of an inputted signal (voltage) on channel 1 of the oscilloscope. Two of three curves are vertically shifted by 400 mV and 800 mV, respectively, for convenience. In each data, there is a different signal contaminating in probe light pulse signals in a region from 0 ns to several tens of nanosecond. Those contamination signals arise from fluorescence from the TPP. This fluorescence, because of being caused only by the pump light, always appears at the same temporal location regardless of positions of the probe light pulses. As signal level just before the rise of each probe light signal should be baseline (white circle in FIG. 7A), it is understood that the actual signal value (solid circle in FIG. 7A) is the value of an emission signal. Accordingly, picking up these signals and repeating this procedure for multiple triggers allow the wave shape of the emission signal to fill the time axis in a random fashion and almost completely be reproduced.

Figure 8:
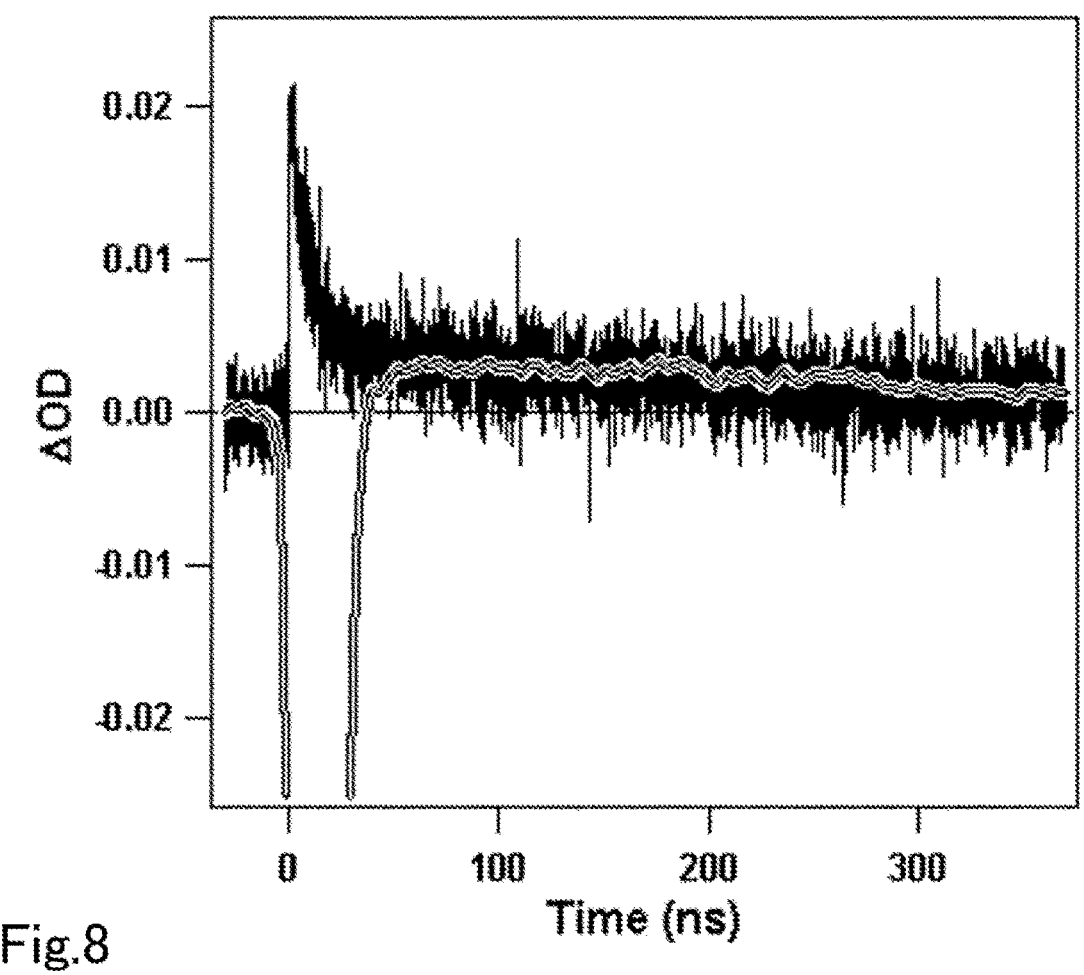
FIG. 8 is a graph showing a waveform reconstructed from the waveform shown in FIG. 7.

The solid curve in FIG. 7B shows the emission signal waveform generated in this way. By large number of triggers (500 times in FIG. 7B), a very smooth curve was obtained. FIG. 7C picks up one of waveforms shown in FIG. 7A and illustrates how fluorescence is removed by expanding time axis around −40 ns to 80 ns. FIG. 7D shows waveforms of probe pulse train after the removal of the emission signal from the waveforms shown in FIG. 7A. As shown in FIG. 7D, it was verified that an emission signal can be obtained and removed from data themselves measured without blocking the probe light, namely, with irradiating both the probe light and pump light. This fact is very valuable in terms of hardware, measurement time and quality of the removal of the emission signal. FIG. 8 clearly shows this conclusion.

In FIG. 8, two curves are overlaid; a solid curve shows a transient absorption waveform reconstructed from the fluorescence—free waveform shown in FIG. 7D, and a multiple black-and-white curve shows a transient absorption waveform obtained by a commercial system based on the CW probe method (TSP-1000, Unisoku). The horizontal axis indicates time, and the vertical axis indicates ΔOD. As the multiple black-and-white curve shows, a positive transient absorption signal supposedly corresponding to decay of a triplet state with a lifetime of an order of several 100 ns is observed normally after 50 ns in the CW probe method, while contamination of a large negative signal due to the emission signal is observed as a false transient absorption signal, which completely prevents information within this time region from being obtained. In other words, the region of up to 50 ns is the gap time region in this data obtained by the CW probe method. On the other hand, in the verification system according to the present invention, in spite that significant emissions were mixed in the obtained data as shown by the waveforms in FIG. 7A, rapid rise within 0.5 ns and a positive signal decaying with a time constant of 8 ns were obtained in the time domain of up to 50 ns in the waveform reconstructed after the removal of the emission signal as shown by the solid curve in FIG. 8. As for TPP, a component with lifetime of several nanoseconds is observed by other experiments, and hence this positive signal is thought to be S1-Sn absorption and its decay in the TPP. In other words, return from an excited singlet state to the ground state in which fluorescence emission accompanies and intersystem crossing to an excited triplet state in the TPP are thought to be observed. In conclusion, it was verified by use of the verification system that the emission signal was precisely extracted and removed almost completely.

4. Another Embodiment (Configuration of Recording Part)

The delay time measurement device 17 and the probe light intensity recorder/accumulator 13 may be substituted together by an oscilloscope as adopted in the verification system. However, since high speed sampling is required to measure rising time from an output signal of the high-speed probe light pulse detector 15 (sampling time was 400 ps in the verification experiments), 5,000 point sampling per channel is executed to obtain a signal for a pulse train of 40 pulses, i.e., a signal up to 2000 ns, which results in a very large amount of data if they are recorded separately for 2,500 trigger events. Thus, for the measurement in a long time range, it is desirable to record minimum necessary signal values in the memory by using A/D converters which are synchronized with the probe light pulse from the probe light source 3. If the A/D converters synchronized with the probe light pulse from the probe light source 3 are employed, with respect to the waveform of a signal output from the probe light intensity detector 11, only two values, i.e., peak intensity and the value immediately before the rising of the pulse waveform mentioned above under the title 3 are A/D converted and recorded. For example, the following may be performed. An output signal is divided into two signals, a signal in an early time region is recorded on the oscilloscope, a signal in a long time region is recorded on A/D converters having memories which are synchronized with the probe light pulse from the probe light source 3, and those data are analyzed, then combined later to reconstruct a transient absorption curve.

5. Still Other Embodiments

FIGS. 9A to 9D show examples of the configurations of the probe light source and the pump light source according to still other embodiments. FIGS. 9A and 9B show configurations according to the other embodiments, FIG. 9C is a block diagram showing the configuration according to the above-described embodiment as a comparative example, and FIG. 9D is a waveform chart schematically illustrating the temporal relationship between the pump light pulse and the probe light pulse in the case of FIG. 9B. The delay generator in FIGS. 9A and 9B corresponds to one of the components in the pump light source or the probe light source according to the present invention.

In the configuration shown in FIG. 9A, time delay is generated based on the pump light source 1, and the probe light source 3 is synchronized with the same. In the configuration shown in FIG. 9B, time delay is generated based on the probe light source 3, and the pump light source 1 is synchronized with the same. In the configuration shown in FIG. 9C, the probe light source 3 and the pump light source 1 are independent of and asynchronous with each other. It can be considered which configuration is appropriate depending on the repetition frequencies in the light sources 1 and 3 or the ratio of the frequencies. Waveforms in FIG. 9D, corresponding to one example of the configuration shown in FIG. 9B, show pulses and a time delay in the configuration where the time delay is generated based on the probe light source 3. In this example, a pump light pulse is generated with a delay time of T−Δt from a certain probe light pulse with a repetition interval of the probe light source 3 referred to as T, and thereby, the delay time of t+δt desired between the pump light pulse and the next probe pulse is realized. Here, δt is a jitter of the pump light source, the probe light source or the delay generator. This jitter causes fluctuation in delay time for every pump light pulse. The configuration which uses synchronization is more effective than that which uses the pump light source and the probe light source asynchronously as shown in FIG. 9C when the repetition frequency of the probe light source 3, f_probe, is not very large compared with that of the pump light source 1, f_pump. For example, when f_probe=10 kHz and f_pump=1 kHz, 10 probe light pulses can be used maximally for one pump light pulse. In this case, an asynchronous configuration as shown in FIG. 9C will require relatively long collection time to obtain high time density of data between 0 to 100 µs since the repetition interval of the probe light is 100 µs. Therefore, as described above, by synchronizing the pump light source 1 and the probe light source 3, controlling delay times, and utilizing jitter positively although the jitter is normally a problem, the delay time can be fluctuated for every pump light pulse, and the time density can be enriched in any of desired time regions (for example, in the gap time region). Generally, it is difficult to make jitter small, whereas it is easy to make jitter large, in particular, by use of the delay generators (for example, for a one-shot multivibrator typical as a delay circuit, 74LS123 with poor accuracy may be used rather than a high-precision multivibrator, 74HC4538.). In any of configurations shown in FIG. 9A and FIG. 9B, a complicated and expensive control unit is not required to control the delay.

6. Advantage of the Present Invention

From the explanation hereinbefore, it is understood that the present invention has the following outstanding advantages.

(1) The pump light source 1 and the probe light source 3 can be independent, and thereby they can be widely selected from various type of light sources. For example, as the pump light source 1, a subnanosecond microchip laser, a diode-laser-excited picosecond Nd: YAG laser, a nitrogen laser, a femtosecond laser with a regenerative amplifier plus a wavelength converter, etc. can be employed. Also, as the probe light source 3, a broadband (white light) Supercontinuum light source, a picosecond laser diode, a mode-locked titanium sapphire laser, a titanium sapphire laser plus a wavelength converter, etc. can be employed. Any combination of those pump light sources 1 and probe light sources 3 can be chosen.

(2) The pump light source 1 and the probe light source 3 can be independent, and the timings of pulse generation can be asynchronous, and hence, a delay generator or the like for controlling both the light sources 1 and 3 so as to make them actively synchronous is not required. We only have to measure delay times between pump light pulses and the first probe light pulses passively and record the measured delay times. Since the delay times are measured passively, large jitter that a pump light source with lower repetition frequency may have does not matter in the measurement.

(3) As mentioned above under the title 3, emission signals like fluorescence can be removed effectively without blocking the probe light, and a pure transient absorption curve can be obtained.

(4) Time range from 100 ps to millisecond can be measured at the same time. The present invention is a technique that fills a gap time region between a conventional CW probe method and a conventional pump probe method. In addition, measurements can be performed even in a time region up to the repetition interval of the pump light. Accordingly, combined with the high removability of emission signal, the single system can not only measure lifetime of an excited singlet sate which cannot be observed by the CW probe method but also explore a long photochemical process following the singlet state.

(5) Data collection time for monochromatic measurements can significantly be shorten.

According to the present invention, e.g. 10, 100, 1000, 10000, or, more probe light pulses can be irradiated on the sample 5 for one pump light pulse. This fact in particular means that the collection time for monochromatic measurements can significantly be reduced compared to that in conventional methods. The present invention is also applicable for a multiple-wavelength simultaneous measurement that does not use a pre-dispersive monochromator, and is not limited to use for the single wavelength measurement. For this application, for example, a multichannel detector which can discriminate multiple wavelengths of a probe pulse train having repetition frequency f, at the same time, can be used.

(6) Applicable wavelength range of probe light is wide.

As the probe light source 3, one with a pulse width of an order of subnanosecond and a repetition frequency of an order of MHz has been known. This type of probe light source 3 can be applied to the present invention together with a detector which can discriminate the neighboring probe pulses. For example, by employing infrared light converted in wave length from a mode-locked picosecond laser and a high speed MCT detector, the present invention is applicable to measurements in a mid-infrared region, and also to measurements in an X-ray region like XAFS. In this respect, the present invention makes a clear contrast with the one which employs the streak camera (used for a CW probe method) of which the wavelength coverage is restricted.

(7) Cost and size can be reduced compared with conventional methods.

Since the transient absorption measurement technique according to the present invention not only fills a gap time region but also covers both time ranges of the CW (continuous wave light) probe methods and pump-probe methods, the technique does not need to employ both the methods to cover a wide time range. Also, as mentioned above, exceptionally complicated and expensive equipment is not required for measurement in the gap region. Furthermore, as noted above, the pulse generation can be asynchronous between the pump source 1 and the probe light source 3, which allows a device for timing adjustment to be omitted.

Thus, the transient absorption measurement technique according to the present invention reduces cost and size of an apparatus.

The present application is based on Japanese Patent Application No. 2014-106109 filed to Japan by the present applicant on May 22, 2014, and all the contents thereof are incorporated herein by reference.

The above description regarding the particular embodiments of the present invention is provided for the purpose of exemplification. Those do not intend to be all-inclusive or to limit the present invention to the described modes. It is obvious for those skilled in the art that a large number of modifications and changes can be made under the contents described above.

DESCRIPTION OF REFERENCE SIGNS

1: Pump light source
3: Probe light source
5: Sample
7: Monochromator (light introduction path)
9: High-speed pump light pulse detector (high-speed pump light pulse detector)
11: Probe light intensity detector (probe light pulse detector; light intensity detector)
13: Probe light intensity recorder/accumulator (probe light intensity recorder)
15: High-speed probe light pulse detector
17: Delay time measurement device (probe light intensity recorder)
19: Reference probe light intensity detector
21: Control unit (image data generator)
BS1-BS3 Beam splitters (light introduction path)
L1: Lens (light introduction path)

The invention claimed is:

1. A transient absorption measurement method comprising:
    providing a pump light source for repeatedly generating a pump light pulse;
    providing a probe light source for repeatedly generating a probe light pulse in a shorter repetition time interval than the pump light pulse, the probe light pulse having a delay time with respect to the pump light pulse shifting every time the pump light pulse is generated;
    providing a sample;
    repeatedly irradiating the pump light pulse on the sample by use of the pump light source;
    repeatedly irradiating the probe light pulse on the sample every time the pump pulse is irradiated;
    detecting an intensity of a probe light pulse having passed through the sample;
    measuring, every time the pump light pulse is irradiated, a shift in a delay time of the probe light pulse with respect to the pump light pulse occurring every time the pump light pulse is generated; and
    obtaining transient absorption measurement data of the sample based on detected data of the probe light pulse intensity obtained in higher time density than repetition time density of the probe light pulse and based on the shift in the delay time measured every time the pump light pulse is irradiated, wherein
    the pump light source and the probe light source are independent of each other and generate the pump light pulse and the probe light pulse in a manner asynchronous with each other.

2. A transient absorption measurement method comprising:

providing a pump light source for repeatedly generating a pump light pulse;

providing a probe light source for repeatedly generating a probe light pulse in a shorter repetition time interval than the pump light pulse, the probe light pulse having a delay time with respect to the pump light pulse shifting every time the pump light pulse is generated;

providing a sample;

repeatedly irradiating the pump light pulse on the sample by use of the pump light source;

repeatedly irradiating the probe light pulse on the sample every time the pump pulse is irradiated;

detecting an intensity of a probe light pulse having passed through the sample;

measuring, every time the pump light pulse is irradiated, a shift in a delay time of the probe light pulse with respect to the pump light pulse occurring every time the pump light pulse is generated; and obtaining transient absorption measurement data of the sample based on detected data of the probe light pulse intensity obtained in higher time density than repetition time density of the probe light pulse and based on the shift in the delay time measured every time the pump light pulse is irradiated, wherein the detection of an intensity of a probe light pulse having passed through the sample is performed by use of a light intensity detector for detecting intensity of light, the transient absorption measurement method further comprises detecting a background light intensity which is a light intensity detected by the light intensity detector repeatedly at a time in a space between repeated irradiations of the probe light pulse without blocking the probe light pulse, and the transient absorption measurement data is obtained through correction that subtracts, from the detected data of the probe light pulse intensity, a detected data of the background light intensity at a corresponding time.

3. The transient absorption measurement method according to claim 2, wherein the pump light source and the probe light source are independent of each other and generate the pump light pulse and the probe light pulse in a manner asynchronous with each other.

4. A transient absorption measurement apparatus comprising:

a pump light source for repeatedly generating a pump light pulse;

a probe light source for repeatedly generating a probe light pulse in a shorter repetition time interval than the pump light pulse, the probe light pulse having a delay time with respect to the pump light pulse shifting every time the pump light pulse is generated to thereby repeatedly generate the probe light pulse every time the pump light pulse is generated;

a light introduction path for introducing the pump light pulse generated by the pump light source and the probe light pulse generated by the probe light source to a sample;

a pump light pulse detector for detecting the pump light pulse;

a probe light pulse detector for detecting the probe light pulse, the probe light pulse detector including a probe light intensity detector for detecting an intensity of the probe light pulse having passed through the sample; and a probe light intensity recorder for repeatedly recording, every time the pump light pulse is detected by the pump light pulse detector, each of intensities of a train of probe light pulses detected by the probe light intensity detector within a certain period crossing an origin time which is a time when the pump pulse is detected, in association with a corresponding one of probe light pulse time data which express times when the probe light pulse detector detects the train of probe light pulses with the origin time as a basis, and thereby accumulating the detected intensities of the probe light pulses within the certain period crossing the origin time in higher time density than repetition time density of the probe light pulse, wherein the pump light source and the probe light source are independent of each other and generate the pump light pulse and the probe light pulse in a manner asynchronous with each other.

5. The transient absorption measurement apparatus according to claim 4, wherein the probe light source generates the probe light pulse at a constant frequency, the probe light pulse detector includes a high-speed probe light pulse detector for detecting the probe light pulse with higher time accuracy than the probe light intensity detector, the pump light pulse detector is a high-speed pump light pulse detector for detecting the pump light pulse with higher time accuracy than the probe light intensity detector, the probe light intensity recorder includes a delay time measurement device for measuring, in response to detection of the pump light pulse by the high-speed pump light pulse detector as a trigger, a period until the high-speed probe light pulse detector, thereafter, firstly detects the probe light pulse, and the probe light pulse time data include the period measured by the delay time measurement device and an order in which the probe light detector detects the train of probe light pulses.

6. The transient absorption measurement apparatus according to claim 4, further comprising an image data generator for generating image data expressing differences, ratios or logarithms of ratios between intensities of a train of probe light pulses and an intensity of a probe light pulse preceding the origin time for each pump light pulse as temporal change on a coordinate system having a time axis and a data axis crossing the time axis based on intensities of the train of probe light pulses and the probe light pulse time data for each pump light pulse recorded by the probe light intensity recorder in a manner associating each of the intensities of the train of probe light pulses with a corresponding one of the probe light pulse time data.

7. A transient absorption measurement apparatus comprising:

a pump light source for repeatedly generating a pump light pulse;

a probe light source for repeatedly generating a probe light pulse in a shorter repetition time interval than the pump light pulse, the probe light pulse having a delay time with respect to the pump light pulse shifting every time the pump light pulse is generated to thereby repeatedly generate the probe light pulse every time the pump light pulse is generated;

a light introduction path for introducing the pump light pulse generated by the pump light source and the probe light pulse generated by the probe light source to a sample;

a pump light pulse detector for detecting the pump light pulse;

a probe light pulse detector for detecting the probe light pulse, the probe light pulse detector including a probe light intensity detector for detecting an intensity of the probe light pulse having passed through the sample; and a probe light intensity recorder for repeatedly recording, every time the pump light pulse is detected by the pump light pulse detector, each of intensities of a train of probe light pulses detected by the probe light intensity detector within a certain period crossing an origin time which is a time when the pump pulse is detected, in association with a corresponding one of probe light pulse time data which express times when the probe light pulse detector detects the train of probe light pulses with the origin time as a basis, and thereby accumulating the detected intensities of the probe light pulses within the certain period crossing the origin time in higher time density than repetition time density of the probe light pulse, wherein the probe light intensity recorder further records a background light intensity detected by the probe light intensity detector repeatedly at a time in a space between repeated irradiations of the probe light pulse without blocking the probe light pulse within at least an initial certain period on and after the origin time for each pump light pulse, in association with a background light detection time data which expresses the time in the space with the origin time as a basis, the transient absorption measurement apparatus further comprises an operation unit that subtracts, from each of the intensities of the train of probe light pulses for each pump light pulse, the background light intensity at a corresponding time to obtain corrected intensities of the train of probe light pulses based on (i) the intensities of the train of probe light pulses and the probe light pulse time data for each pump light pulse recorded by the probe light intensity recorder in a manner of association and (ii) the background light intensities within the at least initial certain period and the background light detection time data for each pump light pulse recorded by the probe light intensity recorder in a manner of association, and obtains transient absorption measurement data of the sample based on the corrected intensities of the train of probe light pulses.

8. The transient absorption measurement apparatus according to claim 7, wherein
the pump light source and the probe light source are independent of each other and generate the pump light pulse and the probe light pulse in a manner asynchronous with each other.

9. The transient absorption measurement apparatus according to claim 7, wherein the operation unit comprises an image data generator for, based on (i) the intensities of the train of probe light pulses and the probe light pulse time data for each pump light pulse recorded by the probe light intensity recorder in a manner of association and (ii) the background light intensities within the at least initial certain period and the background light detection time data for each pump light pulse recorded by the probe light intensity recorder in a manner of association, generating image data expressing differences, ratios or logarithms of ratios between the corrected intensities of the train of probe light pulses obtained by subtracting, from each of the intensities of the train of probe light pulses for each pump light pulse, the background light intensity at a corresponding time and the intensity of the probe light pulse preceding the origin time as temporal change on a coordinate system having a time axis and a data axis crossing the time axis.

10. The transient absorption measurement apparatus according to claim 4, further comprising a reference probe light intensity detector for detecting, as a reference probe light pulse intensity, an intensity of the probe light pulse before passing through the sample, wherein
the probe light intensity recorder further records, together with each of the intensities of the train of probe light pulses detected by the probe light intensity detector, a corresponding reference probe light pulse intensity detected by the reference probe light intensity detector in association with a corresponding one of the probe light pulse time data.

11. The transient absorption measurement apparatus according to claim 10, further comprising an image data generator for, based on the intensities of the train of probe light pulses, the reference probe light pulse intensity and the probe light pulse time data for each pump light pulse recorded by the probe light intensity recorder in a manner of association, generating image data expressing differences, ratios or logarithms of ratios between (i) corrected intensities obtained by correcting each of the intensities of the train of probe light pulses for each pump light pulse by a corresponding reference probe light pulse intensity and (ii) a corrected intensity obtained by correcting the intensity of the probe light pulse proceeding the origin time by a corresponding reference probe light pulse intensity as temporal change on a coordinate system having a time axis and a data axis crossing the time axis.

12. The transient absorption measurement apparatus according to claim 7, further comprising a reference probe light intensity detector for detecting, as a reference probe light pulse intensity, an intensity of the probe light pulse before passing through the sample, wherein
the probe light intensity recorder further records, together with each of the intensities of the train of probe light pulses detected by the probe light intensity detector, a corresponding reference probe light pulse intensity detected by the reference probe light intensity detector in association with a corresponding one of the probe light pulse time data.

13. The transient absorption measurement apparatus according to claim 12, further comprising an image data generator for, based on the intensities of the train of probe light pulses, the reference probe light pulse intensity and the probe light pulse time data for each pump light pulse recorded by the probe light intensity recorder in a manner of association, generating image data expressing differences, ratios or logarithms of ratios between (i) corrected intensities obtained by correcting each of the intensities of the train of probe light pulses for each pump light pulse by a corresponding reference probe light pulse intensity and (ii) a corrected intensity obtained by correcting the intensity of the probe light pulse proceeding the origin time by a corresponding reference probe light pulse intensity as temporal change on a coordinate system having a time axis and a data axis crossing the time axis.

* * * * *